United States Patent [19]

Harwin

[11] Patent Number: 5,163,961
[45] Date of Patent: Nov. 17, 1992

[54] COMPRESSION-FIT HIP PROSTHESIS AND PROCEDURES FOR IMPLANTATION THEREOF

[76] Inventor: Steven F. Harwin, 1050 Park Ave., New York, N.Y. 10021

[21] Appl. No.: 686,759

[22] Filed: Apr. 17, 1991

[51] Int. Cl.⁵ .............................................. A61F 2/32
[52] U.S. Cl. ................................................... 623/23
[58] Field of Search ........................ 623/16, 18, 20, 22, 623/23

[56] References Cited

U.S. PATENT DOCUMENTS

| | | | |
|---|---|---|---|
| 2,668,531 | 2/1954 | Haboush | 623/18 |
| 2,765,787 | 10/1956 | Pellet | 623/18 |
| 3,528,109 | 1/1968 | Scales | 623/18 |
| 3,670,724 | 6/1972 | Bosacco | 623/18 |
| 3,685,058 | 8/1972 | Tronzo | 623/23 |
| 3,781,917 | 1/1974 | Mathys | 623/23 |
| 3,782,373 | 1/1974 | Smythe | 623/23 |
| 3,843,975 | 10/1974 | Tronzo | 623/23 |
| 3,896,504 | 7/1975 | Fischer | 623/23 |
| 4,101,985 | 7/1978 | Baumann et al. | 623/23 |
| 4,153,953 | 5/1979 | Grobbelaar | 623/23 |
| 4,698,063 | 10/1987 | Link et al. | 623/23 |
| 4,778,473 | 10/1988 | Matthews et al. | 623/23 |
| 4,787,909 | 11/1988 | Frey et al. | 623/23 |
| 4,795,473 | 1/1989 | Grimes | 623/23 |
| 4,840,632 | 6/1989 | Kampner | 623/23 |
| 4,871,368 | 10/1989 | Wagner | 623/23 |
| 4,883,491 | 11/1989 | Mallory et al. | 623/23 |
| 4,895,572 | 1/1990 | Chernoff | 623/23 |
| 4,936,863 | 6/1990 | Hofmann | 623/23 |

OTHER PUBLICATIONS

Grosse & Kempf Femoral Locking Nail System (1986 Annual Product Catalog-Howmedica, p. I-2).
J. Arthroplasty, vol. 5 Supplement, 1990, S15-S20.
J. Arthroplasty, vol. 5 Supplement, 1990 S35-S41.

*Primary Examiner*—David Isabella
*Attorney, Agent, or Firm*—Rosenman & Colin

[57] ABSTRACT

A femur head prosthesis has a curved elongate body for insertion into a femoral intramedullary canal and at least one bore extending downwardly between an entrance opening in the upper lateral region of one side of the body and an exit opening in the lower medial region of the other side, each exit opening being arranged for positioning below the calcar region of a femur; a procedure for implantation thereof; a one-piece molded plastic acetabular component for a hip prosthesis; and a femoral component permitting relative rotation between the ball and stem portions thereof.

20 Claims, 7 Drawing Sheets

COMPRESSION-FIT HIP PROSTHESIS AND PROCEDURES FOR IMPLANTATION THEREOF

The present invention relates to total hip prostheses, and more particularly to an improved femoral component and an improved acetabular component thereof.

Implantations of hip prostheses are now widely available. While these procedures are successful, nevertheless implanted femoral components may give rise to rotational and/or axial micromovement with respect to the axis of the femoral component, which can lead to failure of the arthroplasty. The present invention provides a femoral head prosthesis for femora with and without intact calcar regions that have improved resistance to such micromovements.

In one embodiment, the present invention provides a femoral prosthesis, comprising a curved elongate body for insertion into a femoral intramedullary canal having upper and lower ends, a lateral face for positioning at the greater trochanter of a femur, a medial face including a medial arc for positioning against a calcar arc of a femur and opposed anterior and posterior sides, and at least one bore extending downwardly between an entrance opening located in the upper lateral region of one of the sides and an exit opening located in the lower medial region of the other of the sides, each of said exit openings being arranged for positioning below the calcar region of a femur.

The prosthesis of this first embodiment is implanted by shaping an upwardly extending open cavity in a femur having a calcar region, inserting the prosthesis into the cavity and affixing the prosthesis to the femur by means of a screw passing through one of the bores and exiting into cortical bone below the calcar region.

In another embodiment, the present invention provides a femur head prosthesis, comprising an elongate body for insertion into a femoral intramedullary canal having upper and lower ends, a lateral face for positioning at the greater trochanter of a femur, a stop surface at the medial region of the lower end of the body for positioning on a resected surface at the medial region of a femur and opposed anterior and posterior sides, a stem depending from the lateral region of the body, and at least one primary bore extending downwardly between an entrance opening located in the upper lateral region of one of the sides and an exit opening located in the lower medial region of the other of the sides, each of the exit openings being arranged for positioning adjacent to the cortical bone of a femur.

The prosthesis of this second embodiment is implanted by resecting the remaining portion of the head and neck of a femur lacking a calcar region to expose the interior thereof, providing an upwardly extending open cavity in the femur, resecting the upper medial region of the femur to provide a surface transverse to the axis of the cavity, inserting the prosthesis into said cavity with the stop surface resting on the resected surface, and affixing the prosthesis to the femur by means of a screw passing through one of the primary bores and exiting into cortical bone in the lower medial region of the femur.

It is further preferred when using the second embodiment of the invention to provide at least one secondary bore in the body extending between the sides at the upper lateral region thereof and above the primary bores, whereby a screw can be passed through the secondary bore into cortical bone or soft tissue of the upper lateral region of the femur.

In a further embodiment of the invention, the body of the prosthesis is overcoated with a porous means for promoting bone ingrowth and the upper part of the cavity in the femur is shaped to be slightly smaller than the overcoated body. Preferably, the porous means projects beyond the outer surface of the stem to promote a tighter fit and more rapid bone ingrowth.

In yet a further embodiment of the invention, a one-piece plastic acetabular component is provided having means for enhancing cement bonding of the acetabular component to the bone.

The present invention is illustrated in terms of its preferred embodiments in the accompanying drawings, in which.

Figures 1, 2, 3:
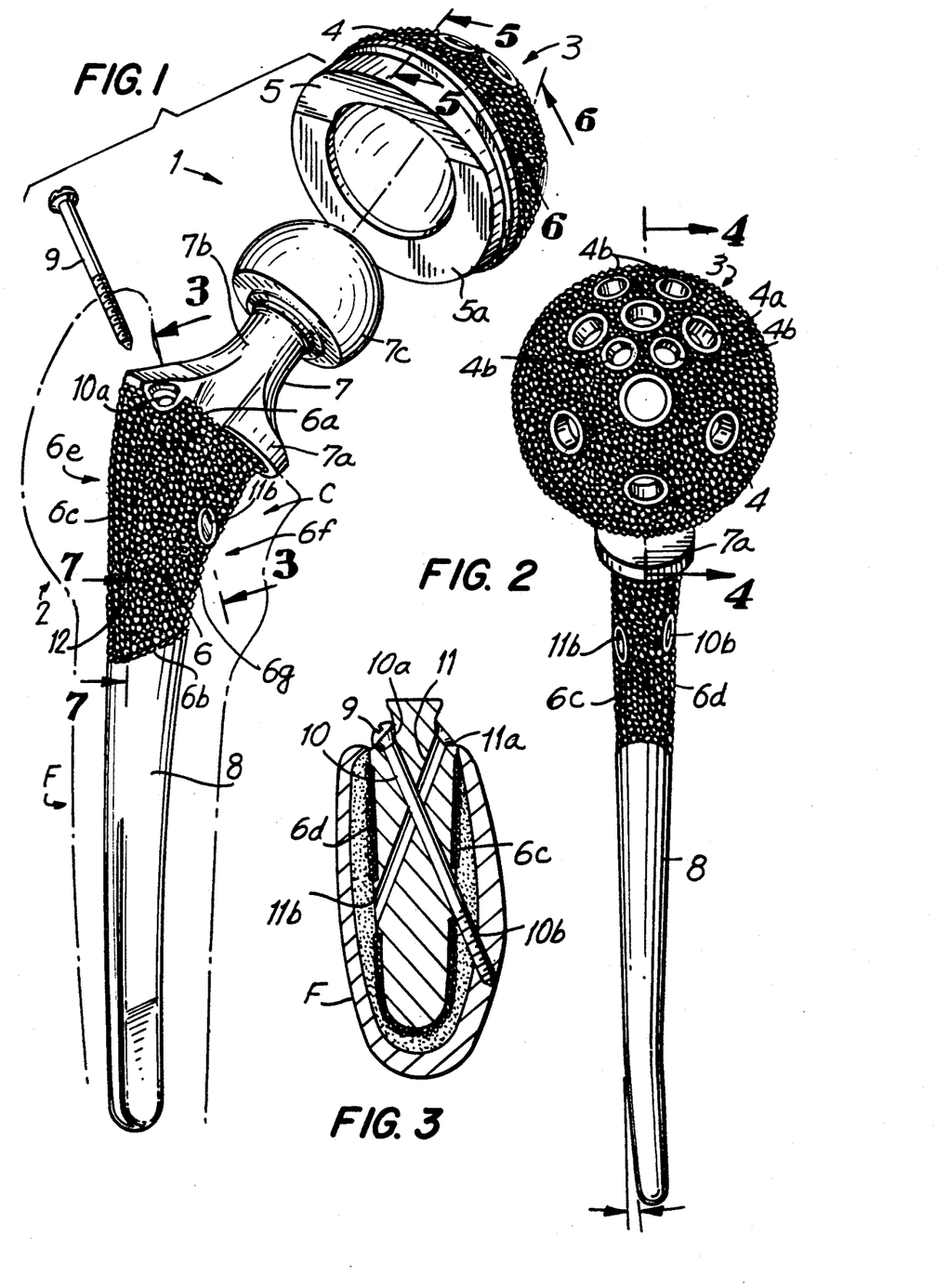
FIG. 1 is an exploded perspective view of the hip prosthesis of the present invention.
FIG. 2 is a side elevational view of the assembled hip prosthesis of the invention.
FIG. 3 is a view in section taken along lines 3—3 of FIG. 1.

Referring to FIG. 1, the total hip prosthesis 1 of the present invention comprises a femoral component 2 for insertion into a femoral intramedullary canal and an acetabular component 3 for attachment to the acetabulum of the pelvis of the patient. The acetabular component 3 comprises a metal cup 4 into which is snap-fit a plastic inner socket 5. The acetabular component 3 will be discussed in more detail hereinafter.

The femoral component 2 comprises a curved elongate body 6 having an upper end 6a and a lower end 6b, and an anterior side 6c and posterior side 6d (FIG. 3). FIG. 1 shows in phantom line a femur F to indicate the relative position of the femoral component 2 when press-fit into a femoral intramedullary canal. In particular, the body 6 has a lateral face 6e (FIG. 1) that is positioned at the greater trochanter of the femur and a medial face 6f, including a medial arc 6g, that is positioned against the calcar arc of the femur.

Projecting from the upper end 6a of the body 6 is a head prosthesis 7, which has a flange or collar 7a projecting away from the medial face 6f and a neck portion 7b projecting from the upper end 6a of the body 6 at an axis inclined to the longitudinal axis of the body 6. Surmounting the neck 7b is a ball 7c that cooperates with the socket 5 of the acetabular component 3.

Figures 11, 12:
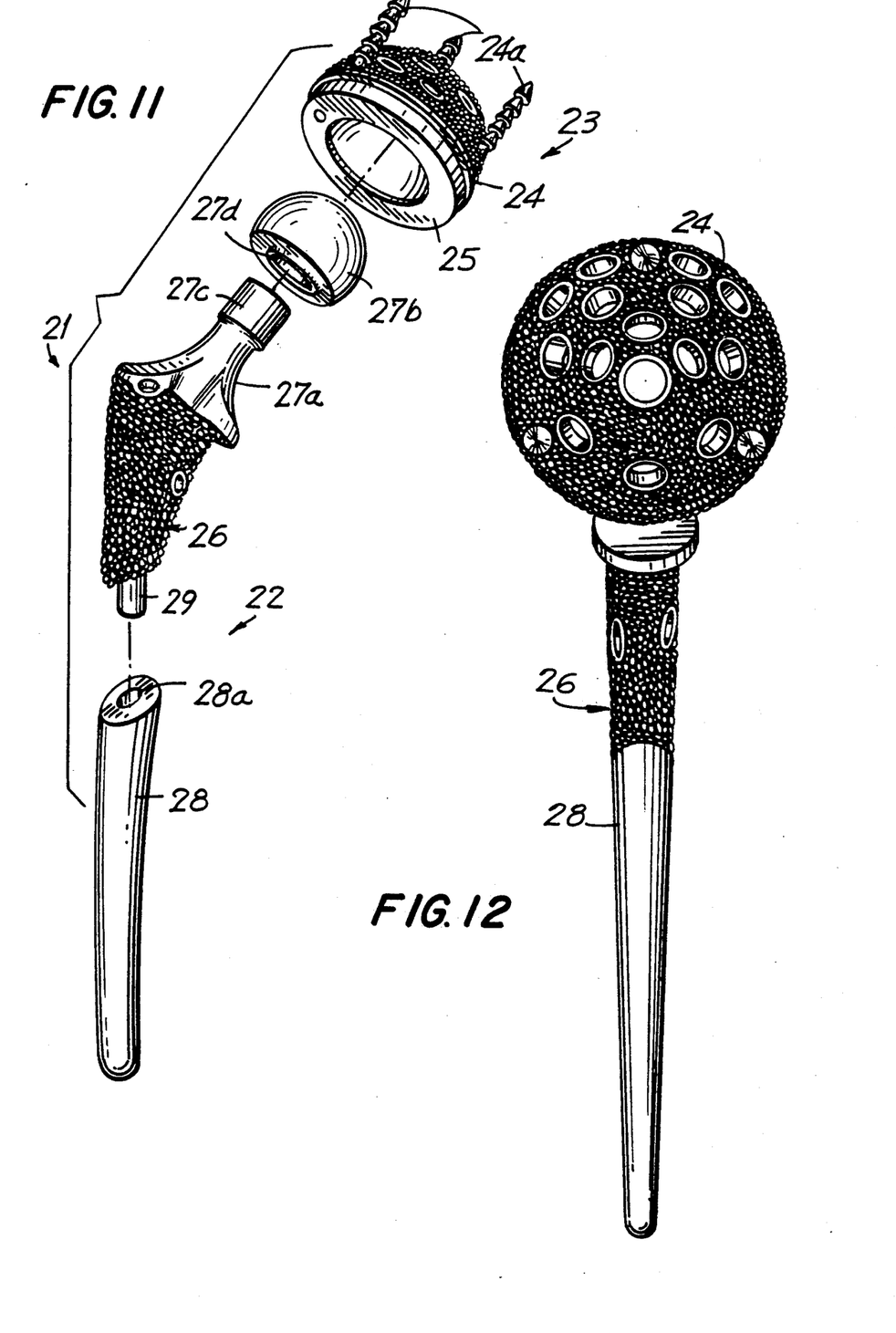
FIG. 11 is an exploded perspective view of an alternative embodiment of the invention.
FIG. 12 is a side elevational view of the assembled hip prosthesis of FIG. 11.

Depending from the lower end 6b of the body 6 is a stem 8. For longer stems of from about 250 mm or more, the stem 8 is preferably provided with an anterior bow (FIG. 2) of about 5° corresponding to the normal anatomy of the femur to accommodate the natural bow of the femur and to provide an improved friction fit into the intramedullary canal of the femur. In the embodiment shown in FIGS. 1-3, the femoral component 2 is of one-piece construction. A modular construction is shown in FIGS. 11 and 12.

Bone screw 9 is used to secure the femoral component 2 to the femur after implantation thereof. To this end, body 6 is provided with two downwardly extending bores 10, 11 between sides 6c, 6d. In particular, bore 10 has an entrance opening 10a in the upper lateral region of anterior side 6c and an exit opening 10b (FIG. 3) in the lower medial region of the posterior side 6d. Conversely, bore 11 has an entrance opening 11a in the upper lateral region of the posterior side 6d and an exit opening 11b in the lower lateral region of the anterior side 6c. As can be seen in FIG. 3, bores 10 and 11 intersect, although it is, of course, possible to arrange them so that they are closely adjacent, but nevertheless not intersecting. After implantation of the femoral component 2 into the femur, the surgeon will select which of bores 10, 11 is more appropriate to use for the bone screw 9.

It is an important feature of the present invention that, when the femoral component 2 is implanted into the femur, the exit openings 10b and 11b will be located below the calcar region C (FIG. 1) of the femur so that the integrity of the calcar region is not violated. The exit openings 10b, 11b are thus located such that the screw 9 exits into and is secured to strong cortical bone near the lesser trochanter. This geometry avoids penetration of the calcar region by screw 9, which would compromise the bony stability and cause fracture.

Engagement of the screw 9 with the bone causes a downward wedging of the femoral component 2 into the intramedullary canal and results in a more secure, tight compression-fit of the femoral component 2 with the femur. In turn, this prevents or at least greatly minimizes micromovement of the femoral component 2 with respect to the femur, both rotational movement about the longitudinal axis of the femoral component 2 as well as axial movement thereof. Moreover, the engagement of the screw 9 into the bone forcefully urges the porous coating 12 into contact with cancellous bone and promotes growth of the cancellous bone into the porous coating 12.

In addition, the downward wedging of the body 6 and stem 8 into the intramedullary canal effected by screw 9 brings the flange or collar 7a into tighter engagement with the bone. Flange 7a, in combination with screw 9, axially stabilizes the femoral component 2 and transfers loads applied to the femoral component 2 to the bone, which minimizes stress shielding.

Figure 14:
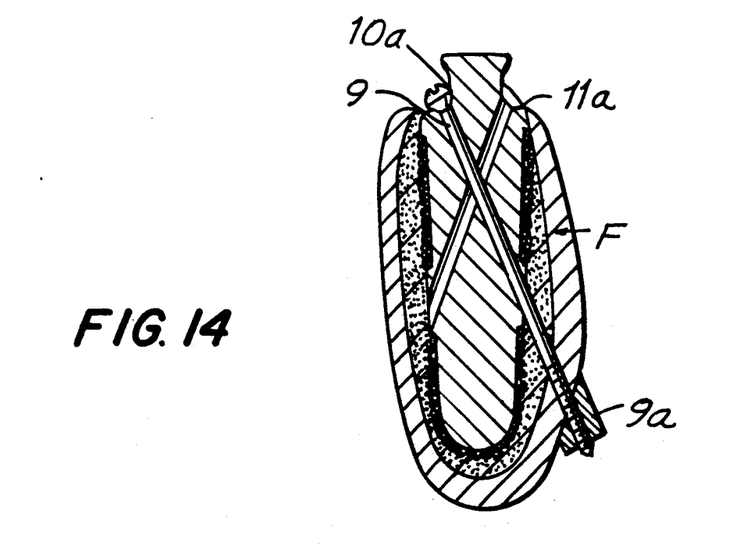
FIG. 14 is a view similar to FIG. 3 showing an alternative means for securing a bone screw in place.

FIG. 14 illustrates an alternative procedure for fastening bone screw 9 in place. Here, the screw 9 is of a sufficient length to pass through the bone, and a nut 9a is used to lag screw 9 into place.

Figure 7:
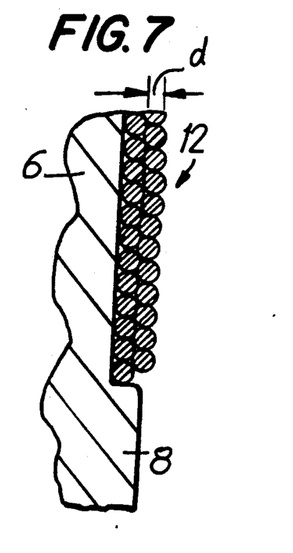
FIG. 7 is a view in section taken along lines 7—7 of FIG. 1.

As shown in FIGS. 1-3, body 6 is preferably overcoated with a porous coating 12 capable of promoting bone ingrowth. This porous coating 12 extends to the underside of the flange 7a. Any suitable porous bone ingrowth coating conventionally used with femoral implants may be used with the femoral implant of the present invention. Alternatively, other enhancers (not shown), such as a hydroxyapatite coating, may be used. With reference to FIG. 7, the bone will be prepared such that the intramedullary canal at the region in which the body 6 is to be placed will be slightly smaller in cross-section than the overcoated body 6 by twice the distance d so that when the body 6 is press fit into the canal, the bone ingrowth coating 12 is forcefully urged into and penetrates the cancellous bone.

While the embodiment of FIGS. 1-3 is presently preferred, a smooth press-fit prosthesis may also be used in the present invention.

Figure 4:
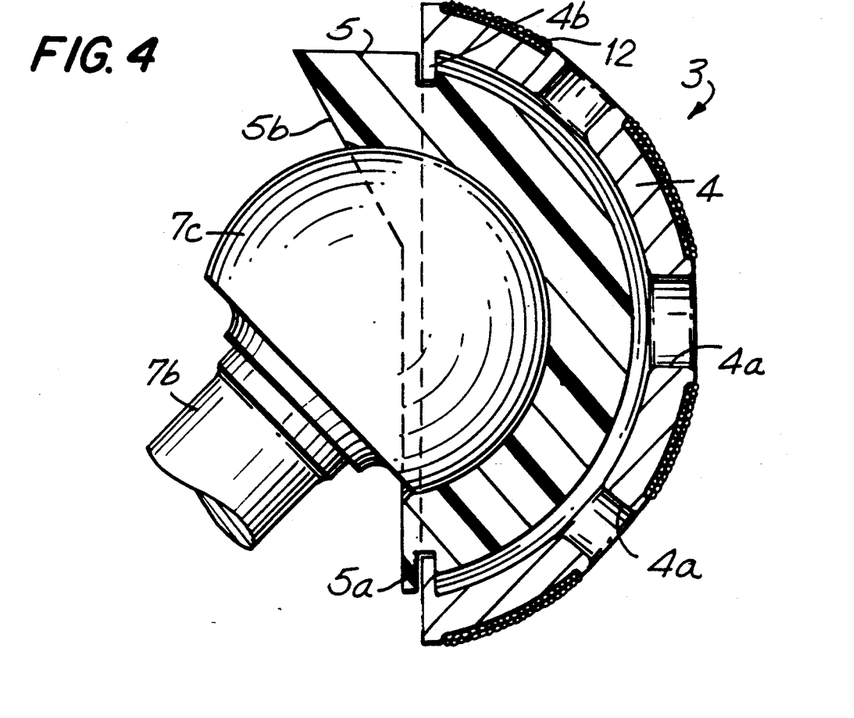
FIG. 4 is a view in section taken along lines 4—4 of FIG. 2.
Figure 5:
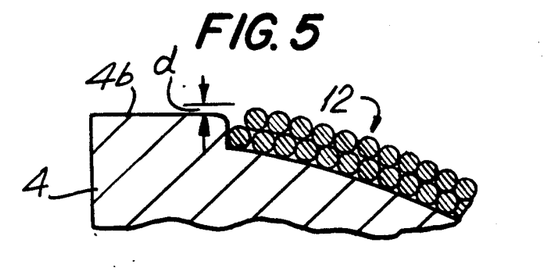
FIG. 5 is a view in section taken along lines 5—5 of FIG. 1.
Figure 6:
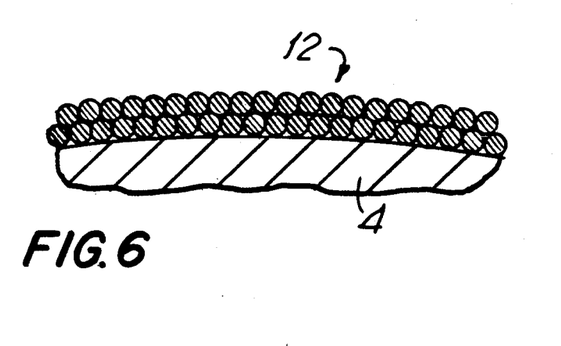
FIG. 6 is a view in section taken along lines 6—6 of FIG. 1.

Referring to FIGS. 4-6, the metal cup 4 of the acetabular component 3 is provided with a plurality of apertures 4a through which the desired number of bone screws (not shown) may be used to fasten the cup 4 to the pelvis, including a group of apertures 4b in the superior dome. The outer surface of cap 4 is provided with a porous coating 12, such as that used for the body 6. Preferably, the porous coating 12 also extends beyond the outer surface 4c of the cup 4 by a distance d, such that the porous coating 12 will penetrate into the cancellous bone of the pelvis when the cup 4 is fixed thereto.

Plastic socket 5 is snap-fitted into the cup 4 and is provided with conventional means to prevent rotation of the socket 5 with respect to the cup 4, such as by providing mating flats (not shown) on the outer surface of the socket 5 and the inner surface of the cup 4. Preferably, the socket 5 is provided with a low profile hood or extension 5b projecting beyond cup 4 at the upper portion of the socket 5 to provide a greater range of mobility for the implanted prosthesis than is obtained with conventional plastic sockets in which the entire rim thereof lies in a common plane closely adjacent to the cup 4. As seen in FIGS. 1 and 4, the socket 5 of the present invention has a rim portion 5a lying in a plane perpendicular to the polar axis of the cup 4, while the asymmetric hood portion 5b projects outwardly from that plane at angle of up to about 15°.

Figure 8:
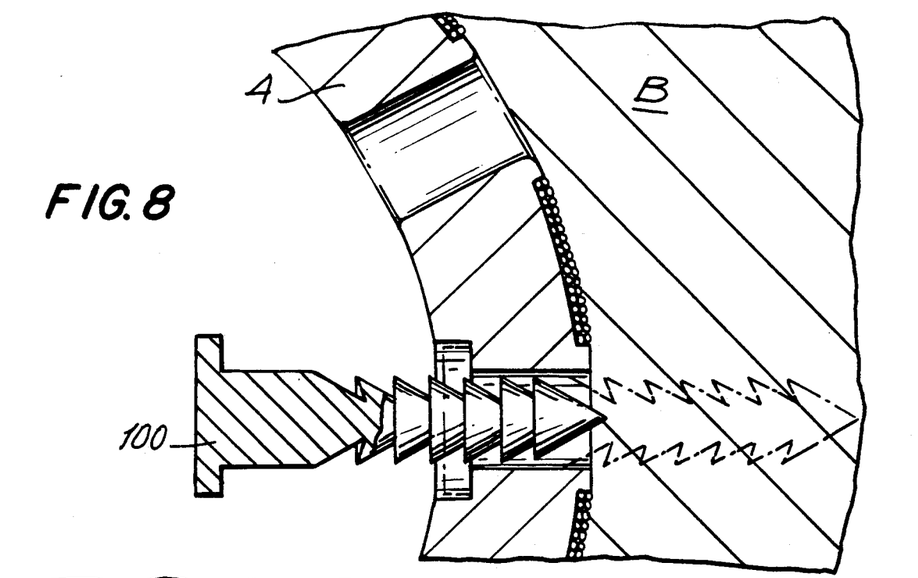
FIGS. 8-10 are detail views, in section, of alternative means for fastening the acetabular component shown in FIG. 1 to the acetabulum.
Figure 9:
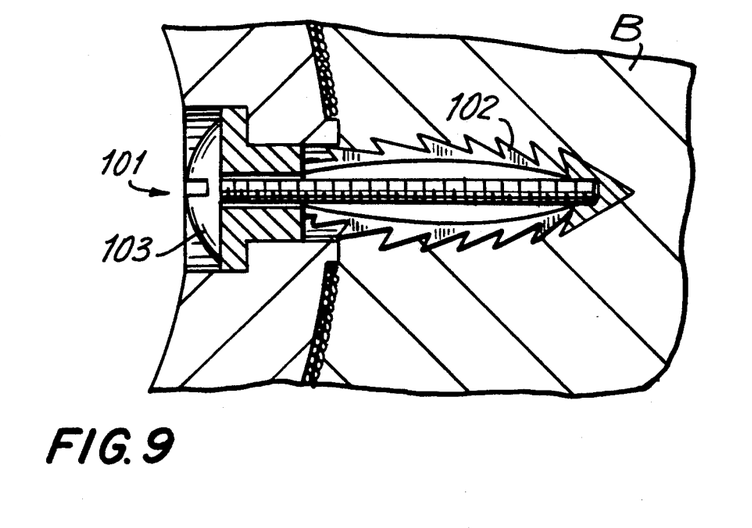
Figure 10:
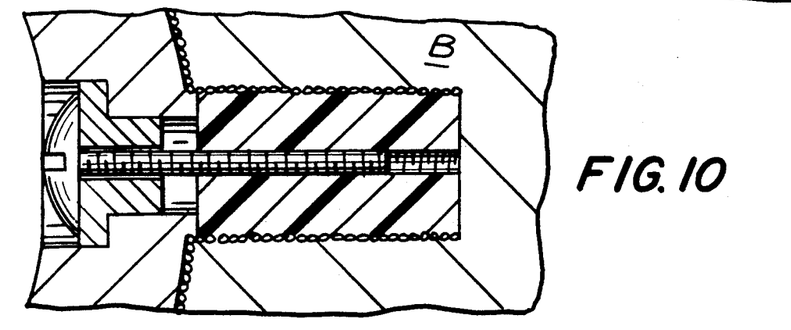

FIGS. 8-10 illustrate alternative means for fixing the cup 4 to the cancellous bone B. In FIG. 8, barbed bone nail 100 is forced into the bone B, while in FIG. 9, a bone nail 101 is used having a barbed portion 102 and a threaded screw portion 103. After insertion of the nail 101 into the bone B, the screw 103 is rotated to cause the barbs 102 to flex away from the screw 103 and forcibly penetrate the cancellous bone tissue B.

FIG. 10 shows a bone screw 104 received in an expandable plastic sleeve 105 having porous coating 12 on its outer surface. When screw 104 is screwed into sleeve 105, the porous coating 12 is forcefully urged into bone B.

FIGS. 11 and 12 illustrate an alternative embodiment of the invention in which modular parts are used. Thus, the prosthesis 21 comprises a femoral portion 22, and an acetabular portion 23 comprising metal cup 24 and plastic socket 25. Projecting from the metal cup 24 are barbed bone staples 24a.

Femoral component 22 comprises body 26 having a neck portion 27a integral therewith. Ball portion 27b is separate from and is press-fit onto end 27c of the neck 27a. End 27c is provided with a Morse taper to obtain secure, fixed attachment of ball 27b to end 27c. Likewise, shank portion 28 is separate from and is press-fit onto post 29 depending from the lower end of body 26. FIG. 12 shows the femoral implant 22 fully assembled with the acetabular component 23 detachably secured thereto.

The use of the modular components shown in FIGS. 11 and 12 permits the practitioner to stock a variety of sizes of bodies 26 and shanks 28, with the recess 28a in shank 28 and post 29 being of a standard size such that the practitioner can press fit a shank 28 of desired length onto the post 29 of the body 26 to accommodate a wide variety of sizes of femoral canals. Similarly, the end 27c and the recess 27d will also be standardized whereby a variety of sizes of balls 27b may be used. This in turn permits the use of a variety of sizes of acetabular components 23. As stated above, it is preferred that the longer stems have a 5° anterior bow.

Figure 13:
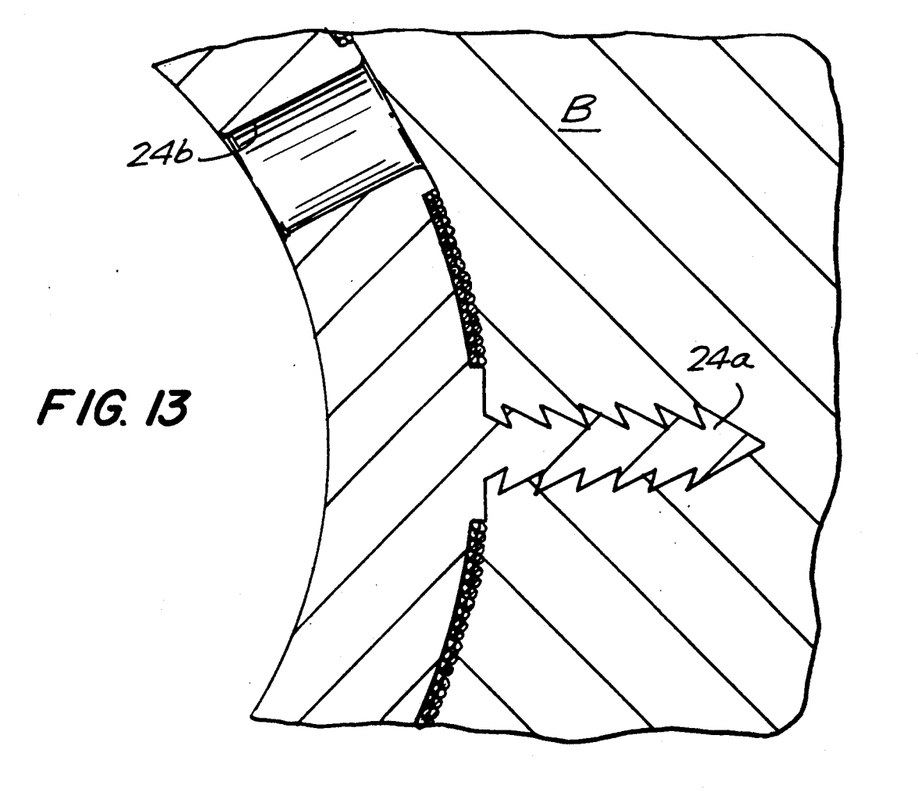
FIG. 13 is a detail view in section showing the acetabular component of the hip prosthesis of FIG. 11 fastened to the acetabulum.

FIGS. 11-13 illustrate an embodiment of the invention in which the acetabular component 23 has barbed bone staples 24a integral therewith. After drilling pilot holes into the bone B, the practitioner can then nail the cup 24 into place using the barbed staples 24a (FIG. 13) whereafter additional bone screws can be inserted into the desired one of the cluster of apertures 24b.

Figures 15, 16:
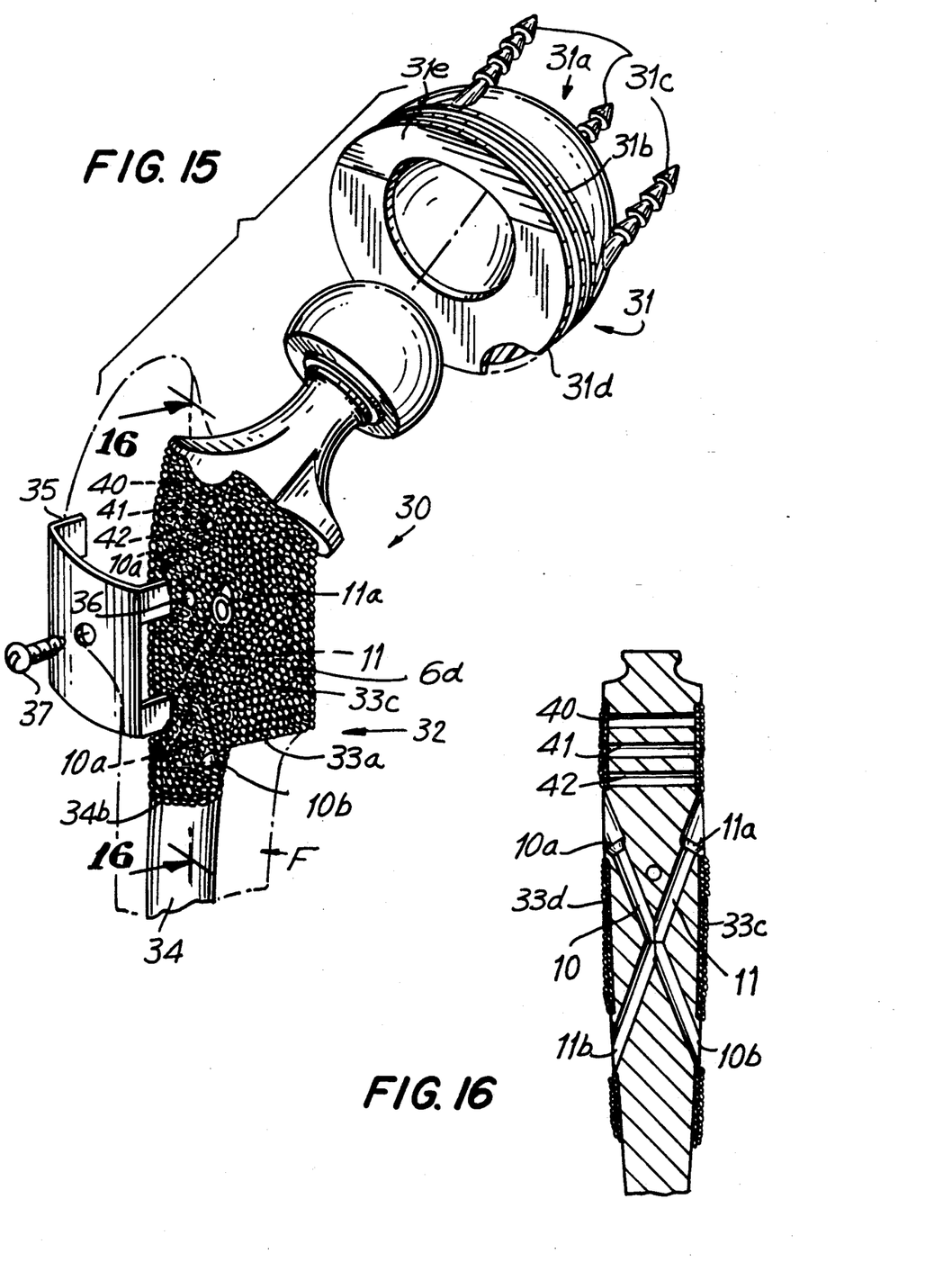
FIG. 15 is an exploded view in prospective of another alternative hip prosthesis of the invention.
FIG. 16 is a view in section taken along lines 16—16 of FIG. 15.

FIG. 15 shows prosthesis 30 having a one piece, all plastic acetabular component 31 and a modified femoral component 32. Although illustrated with the femoral component 32, it is to be understood that the all-plastic acetabular component 31 may be used with any of the femoral components of the present invention or indeed with any conventional femoral component. Acetabular component 31 is intended to be cemented in place.

Acetabular component 31 may be conveniently molded in one piece from any desired tough plastic material, such as nylon, polyethylene and the like. Acetabular component 31 has a generally hemispherical cup 31a having a circumferential groove 31b therein to enhance cement bonding of the cup portion to the bone. While only one groove 31b is shown, it is to be understood that more than one groove may also be used. In addition, the grooves 31b may extend completely or partially around the cup 31a.

Cup 31a is installed by drilling holes in the acetabulum in a pattern corresponding to the integral barbed plastic staples 31c, coating the cup 31a with a conventional cement and forcing the cup 31a into place, with the plastic staples 31c also entering the pre-drilled holes. The plastic staples 31c enhance bonding of the cement between the cup 31a and bone. Flange 31d extends completely around cup 31a and projects slightly beyond the outer surface of cup 31a, for example by about 1 cm or so. Flange 31d pressurizes the cement to enhance cement bonding.

The femoral component 32 will be used where all or a significant part of the lesser trochanter is not available. Thus, elongate body 33 has a surface 33a, preferably a flat surface, transverse to the longitudinal axis of body 33, at the lower medial region for positioning against a complementary resected surface of the femur F, and a stem 34 depending from the lower lateral end 34b of body 33.

A bone screw, such as bone screw 9 (FIG. 1) is used to secure the femoral component 32 to the femur after implantation thereof. To this end, body 33 is provided with two downwardly extending bores 10, 11 between anterior side 33c and posterior side 33d. In particular, bore 10 has an entrance opening 10a in the upper lateral region of posterior side 33d and an exit opening 10b in the lower medial region of the anterior side 33c. Conversely, bore 11 has an entrance opening 11a in the upper lateral region of the anterior side 33c and exit opening 11b in the lower lateral region of the posterior side 33d. Bores 10 and 11 intersect, although it is, of course, possible to arrange them so that they are closely adjacent, but nevertheless not intersecting. Exits 10b, 11b are located below surface 33a adjacent strong cortical bone.

As shown in FIGS. 15 and 16, bores 10, 11 lie in a plane perpendicular to the lateral-medial direction, but this is not strictly necessary. It is sufficient simply that the downwardly extending bores extend between opposite sides 33c, 33d and exit into strong cortical bone. To assist in securing femoral component 32 in place are bores 40, 41, 42 extending between sides 33c, 33d at the lateral region thereof proximal to the greater trochanter.

Clip 35 (FIG. 15) may be used to provide additional support. Thus, clip 35 is installed by drilling a bore (not shown) in the lateral face of the femur in alignment with the threaded bore 36 in body 33 and then lagging clip 35 in place by means of screw 37 passing through clip 35, through the bore in the femur and into threaded bore 36.

Figures 17, 18:
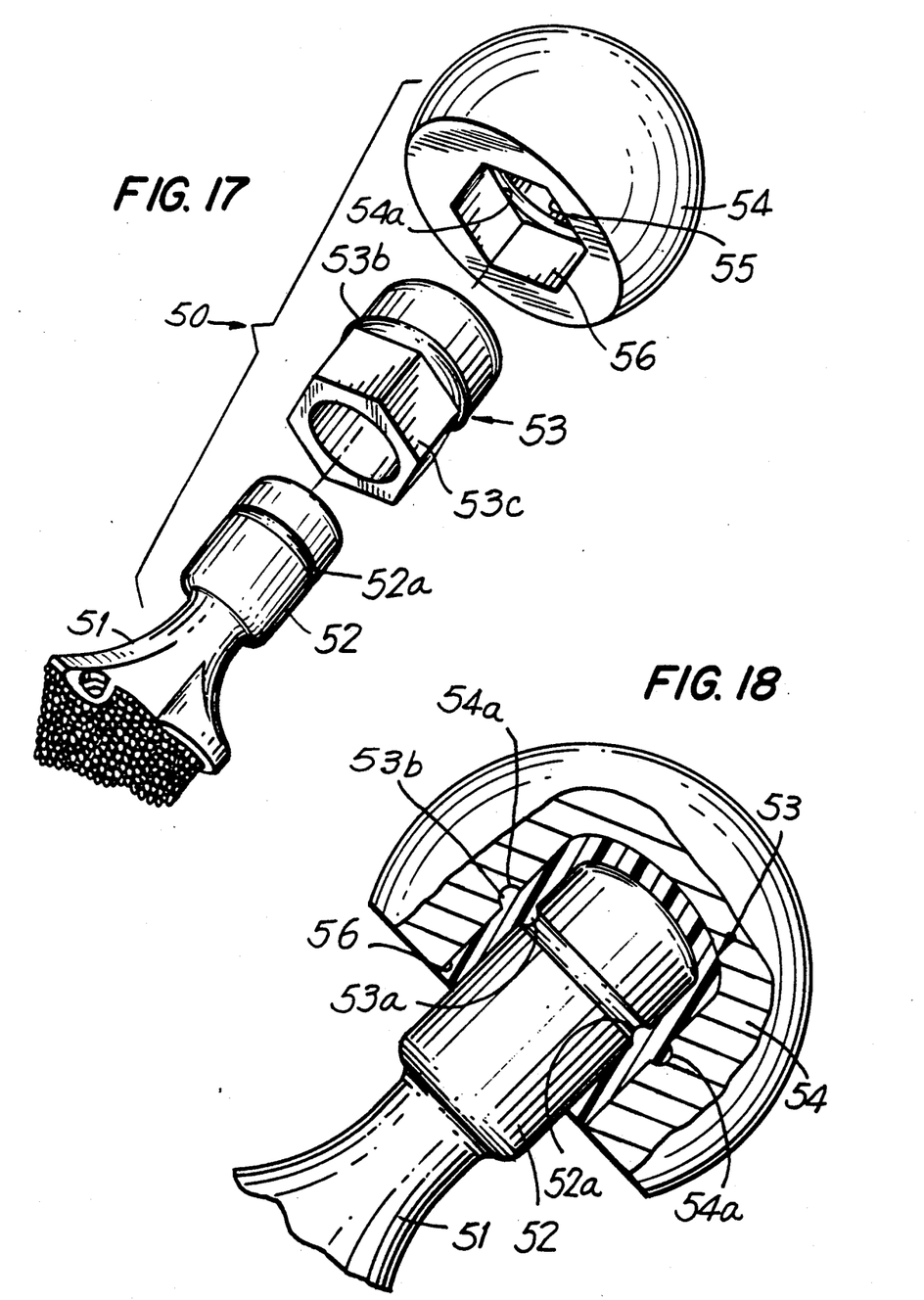
FIG. 17 is an exploded perspective view of an alternative femoral component of the present invention.
FIG. 18 is a view, partly in section, of the assembled femoral component of FIG. 17.

FIG. 17 and 18 show a hip prosthesis 50 comprising a femoral body 51 terminating in a trunion 52 having a circumferentially extending circular groove 52a. Plastic connecting cup 53 has an internal circular ring or rib 53a arranged to snap-fit into groove 52a to prevent cup 53 from sliding axially relative to trunion 52 but permitting relative rotational movement between trunion 52 and cup 53. Ball 54 has an opening 55 having polygonal sides 56 that mate with polygonal sides 53c of cup 53. When cup 53 is inserted into ball 54, external circular ring or rib 53b and snaps into circular groove 54a in ball 54. Ring 53b and groove 54a prevent relative sliding axial movement between cup 53 and ball 54, whereas the complementary sides 53c and 56 prevent relative rotational movement between ball 54 and cup 53. However, since the cup 53 and ball 54 are locked together, the ball 54 can rotate relative to integral body 51 and trunion 52. This introduces greater freedom of movement for femoral component 50 than is obtained with conventional components in which there is no relative rotational movement permitted between the ball and stem portions thereof.

As is known, the metal parts of the various embodiments of the prosthesis of the present invention may be made of any suitable biocompatible high strength material. It is presently preferred to use an alloy of cobalt, chromium and molybdenum for the body, stem and head portions, such as a Vitallium alloy, and metal-backed ultrahigh molecular weight polyethylene for the acetabulum cup. Porous bone ingrowth surface 12 may likewise be provided by known materials. It is presently preferred to form the bone ingrowth surface from an alloy of cobalt, chromium and molybdenum coated to a thickness of about 0.050 inches, such as a Vitallium alloy.

While the femoral components illustrated are of the preferred geometrical shape, other suitable shapes are known and may be used.

The components of the hip prosthesis of the invention may be implanted using known surgical techniques, after which the bone screw 9 is inserted into the desired bore 10 or 11 and secured to the bone. For the preferred embodiment of the invention described above, the medullary canal is shaped to be slightly smaller than the body 6 to cause the porous bone ingrowth coating 12 to penetrate the cancellous bone thereof. In the case of the prosthesis of FIGS. 15 and 16, the medial region of the femur will be resected to provide an appropriate surface, preferably a flat surface, against which the surface 33a will rest.

I claim:

1. A femur head prosthesis, comprising a curved elongate body for insertion into a femoral intramedullary canal having upper and lower ends, a lateral face for positioning at the greater trochanter of a femur, a medial face including a medial arc for positioning against a calcar arc of a femur and opposed anterior and posterior sides, and at least one bore extending downwardly through said body between an entrance opening located in the upper lateral region of one of said opposed sides and an exit opening located in the lower medial region of the other of said opposed sides, each of said exit openings being arranged for positioning below the calcar region of a femur.

2. The prosthesis according to claim 1, wherein said body has a first bore having an entrance opening in the upper lateral region of said anterior side and an exit opening in the lower medial region of said posterior side and a second bore having an entrance opening in the upper lateral region of said posterior side and an exit opening in the lower medial region of said anterior side.

3. The prosthesis according to claim 2, wherein said bores intersect within said body.

4. The prosthesis according to claim 1, wherein said body has a stem depending from said lower end and a head prosthesis projecting from said upper end having an axis inclined to the longitudinal axis of said body.

5. The prosthesis according to claim 4, wherein said stem has a length of at least about 250 mm and has an anterior bow at its lower end.

6. The prosthesis according to claim 4, wherein said head prosthesis has a flange at said upper portion of said body projecting away from said lateral face.

7. The prosthesis according to claim 6, wherein said body is overcoated with a porous means for promoting bone ingrowth, said porous means projecting beyond the outer surface of said stem, and the underside of said flange is also overcoated with a porous means for promoting bone ingrowth.

8. The prosthesis according to claim 4, wherein said body is overcoated with a porous means for promoting bone ingrowth, said porous means projecting beyond the outer surface of said stem.

9. A femur head prosthesis, comprising an elongate body for insertion into a femoral intramedullary canal having upper and lower ends, a lateral face for positioning at the greater trochanter of a femur, a stop surface at the medial region of the lower end of said body for positioning on a resected surface at the medial region of a femur and opposed anterior and posterior sides, a stem depending from the lateral region of said body, and at least one primary bore extending downwardly through said body between an entrance opening located in the upper lateral region of one of said opposed sides and an exit opening located in the lower medial region of the other of said opposed sides, each of said exit openings being arranged for positioning adjacent cortical bone of a femur.

10. The prosthesis according to claim 9, wherein said body has a first primary bore having an entrance opening in the upper lateral region of said anterior side and an exit opening in the lower lateral region of said posterior side and a second primary bore having an entrance opening in the upper lateral region of said posterior side and an exit opening in the lower lateral region of said anterior side.

11. The prosthesis according to claim 10, wherein said bores intersect within said body.

12. The prosthesis according to claim 9, wherein said body has a head prosthesis projecting from said upper end having an axis inclined to the longitudinal axis of said body.

13. The prosthesis according to claim 9, including at least one secondary bore in said body extending between said sides at the upper lateral region thereof and above said primary bores.

14. The prosthesis according to claim 13, wherein a plurality of said secondary bores is provided.

15. A femur head prosthesis according to claim 9, wherein said stem has a threaded bore therethrough with an opening in said lateral face and a cooperating clip means is provided for threaded engagement with said bore.

16. A procedure for implantation of the femur head prosthesis according to claim 1, comprising shaping an upwardly extending open cavity in a femur having a calcar region, inserting said prosthesis into said cavity and affixing said prosthesis to said femur by means of a screw passing through one of said bores and exiting into cortical bone below said calcar region.

17. The procedure according to claim 16, wherein said body of said prosthesis is overcoated with a porous means for promoting bone ingrowth and the upper part of said cavity is shaped to be slightly smaller than said overcoated body.

18. A procedure for implantation of the femur head prosthesis according to claim 9, resecting the remaining portion of the head and neck of a femur lacking a calcar region to expose the interior thereof, providing an upwardly extending open cavity in the femur, resecting the upper medial region of the femur to provide a surface transverse to the axis of said cavity, inserting said prosthesis into said cavity with said stop surface resting on said resected surface, and affixing said prosthesis to said femur by means of a screw passing through one of said primary bores and exiting into cortical bone in the lower lateral region of said femur.

19. The procedure according to claim 18, wherein said body includes at least one secondary bore extending between said sides at the upper lateral region thereof and above said primary bores, and at least one screw is passed through at least one of said bores into cortical bone or soft tissue of the upper lateral region of said femur.

20. The procedure according to claim 18, wherein said body of said prosthesis is overcoated with a porous means for promoting bone ingrowth and the upper part of said cavity is shaped to be slightly smaller than said overcoated body.

* * * * *